(12) United States Patent
Bennett et al.

(10) Patent No.: US 6,232,483 B1
(45) Date of Patent: May 15, 2001

(54) POLYMERIZATION OF ETHYLENE

(75) Inventors: Jordan Lawrence Bennett, Granville, OH (US); Maurice S. Brookhart, III, Chapel Hill, NC (US); Lynda Kaye Johnson, Wilmington, DE (US); Christopher Moore Killian, Gray, TN (US)

(73) Assignee: E. I. du Pont Nemours and Company, Wilmington, DE (US)

( * ) Notice: Subject to any disclaimer, the term of this patent is extended or adjusted under 35 U.S.C. 154(b) by 0 days.

(21) Appl. No.: 09/442,609

(22) Filed: Nov. 18, 1999

Related U.S. Application Data

(62) Division of application No. 09/006,628, filed on Jan. 13, 1998, now Pat. No. 6,060,569.

(60) Provisional application No. 60/035,191, filed on Jan. 14, 1997.

(51) Int. Cl.[7] .............................. C08F 4/60; C07F 15/04
(52) U.S. Cl. ......................... 556/23; 556/21; 556/139; 526/132; 526/172; 526/352
(58) Field of Search ................................ 526/172, 132, 526/352; 556/21, 139, 23

Primary Examiner—Donald R. Wilson
Assistant Examiner—R. Harlan

(57) ABSTRACT

Certain nickel [II] complexes of selected ortho-phosphine substituted arylsulfonamides or selected phosphine containing alkylsulfonamides catalyze the polymerization of ethylene. The polymers produced may be used as lubricants or in waxes. Some of these nickel [II] complexes and the phosphine containing ligands are also novel compounds.

8 Claims, No Drawings

POLYMERIZATION OF ETHYLENE

This is a division of application Ser. No. 09/006,628 filed Jan. 13, 1998, now U.S. Pat. No. 6,060,569.

This application claims the benefit of U.S. Provisional Application No. 60/035,191, filed Jan. 14, 1997.

FIELD OF THE INVENTION

Polymerization of ethylene using as catalysts novel nickel complexes in which the nickel is coordinated to selected phosphorous substituted aryl sulfonamide ligands is described.

TECHNICAL BACKGROUND

Polymers of ethylene are important items of commerce, and these polymers are used in a myriad of ways, from low molecular weight polyethylene (PE) being used as a lubricant and in waxes, to higher molecular weight grades being used for fiber, films, molding resins, etc. In most cases, ethylene is polymerized using a catalyst, often a transition metal compound or complex. These catalysts vary in cost per unit weight of PE produced, the structure of the polymer produced, the possible need to remove the catalyst from the PE, the toxicity of the catalyst, etc. Due to the commercial importance of polymerizing ethylene, new polymerization catalysts are constantly being sought.

P. Braunstein, et al., J. Chem. Soc., Dalton Trans., 1996, p. 3571–3574 report the use of nickel complexes having certain phosphorous-nitrogen ligands as oligomerization catalysts for ethylene. Sulfonamides are not mentioned.

European Patent Application 454,231 discloses certain types of neutral phosphorous ligands in nickel complexes as being useful in olefin polymerizations. Ligands containing sulfonamides are not disclosed.

SUMMARY OF THE INVENTION

This invention concerns a first process for the polymerization of ethylene, comprising, contacting, at a temperature of about −20° C. to about +200° C., ethylene, optionally a Lewis acid, and a compound of the formula

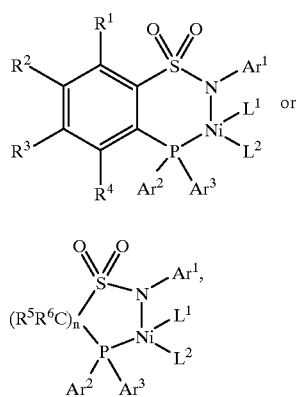

(III)

wherein:
$R^1$, $R^2$, $R^3$ and $R^4$ are each independently hydrogen, hydrocarbyl, substituted hydrocarbyl, or an inert functional group;
$R^5$ and $R^6$ are each independently hydrogen, hydrocarbyl or substituted hydrocarbyl;
n is 1, 2 or 3;

$Ar^1$, $Ar^2$ and $Ar^3$ are each independently hydrocarbyl or substituted hydrocarbyl; and
$L^1$ is a neutral monodentate ligand and $L^2$ is a monoanionic monodentate ligand, or $L^1$ and $L^2$ taken together are a monoanionic bidentate ligand, provided that said monoanionic monodentate ligand or said monoanionic bidentate ligand may be displaced by said ethylene or add to said ethylene.

This invention also concerns a second process for the polymerization of ethylene, comprising contacting, at a temperature of about −20° C. to about +200° C., a Ni [II] complex of a monoanionic bidentate ligand of the formula

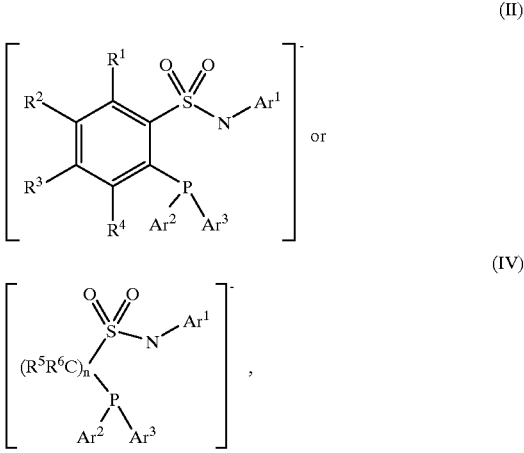

with ethylene and optionally a Lewis acid, wherein:
$R^1$, $R^2$, $R^3$ and $R^4$ are each independently hydrogen, hydrocarbyl, substituted hydrocarbyl, or an inert functional group;
$R^5$ and $R^6$ are each independently hydrogen, hydrocarbyl or substituted hydrocarbyl;
n is 1, 2 or 3;
$Ar^1$ is aryl or substituted aryl;
$Ar^2$ and $Ar^3$ are each hydrocarbyl or substituted hydrocarbyl;
and provided that a Ni [II] atom also has bonded to it a ligand that may be displaced by said ethylene or add to said ethylene.

Also described herein is a compound of the formula

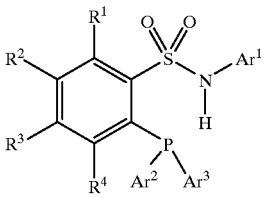

(VIII)

wherein:
$R^1$, $R^2$, $R^3$ and $R^4$ are each independently hydrogen, hydrocarbyl, substituted hydrocarbyl, or an inert functional group;
$R^5$ and $R^6$ are each independently hydrogen, hydrocarbyl or substituted hydrocarbyl;
$Ar^1$ is aryl or substituted aryl; and
$Ar^2$ and $Ar^3$ are each independently hydrocarbyl or substituted hydrocarbyl.

This invention concerns a compound of the formula

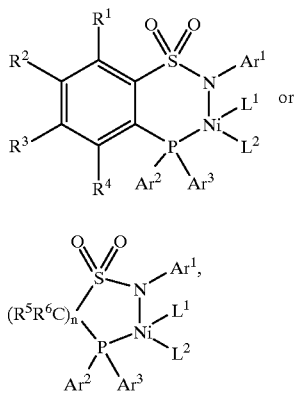

wherein:
- $R^1$, $R^2$, $R^3$ and $R^4$ are each independently hydrogen, hydrocarbyl, substituted hydrocarbyl, or an inert functional group;
- $R^5$ and $R^6$ are each independently hydrogen, hydrocarbyl or substituted hydrocarbyl;
- n is 1, 2 or 3;
- $Ar^1$ is aryl or substituted aryl;
- $Ar^2$ and $Ar^3$ are each independently hydrocarbyl or substituted hydrocarbyl; and
- $L^1$ is a neutral monodentate ligand and $L^2$ is a monoanionic monodentate ligand, or $L^1$ and $L^2$ taken together are a monoanionic bidentate ligand, provided that said monoanionic monodentate ligand or said monoanionic bidentate ligand may be displaced by said ethylene or add to said ethylene.

DETAILS OF THE INVENTION

Herein, certain terms are used. Some of them are:

A "hydrocarbyl group" is a univalent group containing only carbon and hydrogen. If not otherwise stated, it is preferred that hydrocarbyl groups herein contain 1 to about 30 carbon atoms.

By "substituted hydrocarbyl" herein is meant a hydrocarbyl group which contains one or more substituent groups which are inert under the process conditions to which the compound containing these groups is subjected. The substituent groups also do not substantially interfere with the process. If not otherwise stated, it is preferred that substituted hydrocarbyl groups herein contain 1 to about 30 carbon atoms. Included in the meaning of "substituted" are heteroaromatic rings.

By "(inert) functional group" herein is meant a group other hydrocarbyl or substituted hydrocarbyl which is inert under the process conditions to which the compound containing the group is subjected. The functional groups also do not substantially interfere with any process described herein that the compound in which they are present may take part in. Examples of functional groups include halo (fluoro, chloro, bromo and iodo), ether such as —$OR^7$ wherein $R^7$ is hydrocarbyl or substituted hydrocarbyl, nitro and perfluorohydrocarbyl (contains only fluorine and carbon). In cases in which the functional group may be near a nickel atom the functional group should not coordinate to the metal atom more strongly than the groups in compounds which are shown as coordinating to the metal atom, that is they should not displace the desired coordinating group.

By a "polymerization process" herein (and the polymers made therein) is meant a process which produces a polymer with a degree of polymerization (DP) of about 5 or more, preferably about 10 or more (except where otherwise noted) By "DP" is meant the average number of repeat (monomer) units in the polymer.

By "aryl" herein is meant a monovalent radical whose free valence is to a carbon atom of an aromatic ring, preferably a ring carbon atom of a carbocyclic ring. The aryl radical may contain one ring or may contain 2 or more fused rings, such as 9-anthracenyl or 1-naphthyl.

By "substituted aryl" herein is meant an aryl radical substituted with one or more groups that do not interfere with the synthesis of the compound or the resulting polymerization. Suitable substituents include alkyl, aryl such as phenyl, halo, alkoxy, nitro and perfluorohydrocarbyl.

By a "monoanionic ligand" is meant a ligand with one negative charge.

By a "neutral Ligand" is meant is ligand that is not charged.

Compounds useful herein as ligands include (II) and (IV), as described above. The ligands are made from the corresponding sulfonamides. Sulfonamides (II) can be made by reacting an arylsulfonyl chloride with an appropriate aromatic amine (see Experiments B to E). The resulting sulfonamide is then lithiated as with n-butyl lithium and reacted with an appropriate diarylchlorophosphine (see Examples 1 to 5). The sulfonamides corresponding to the ligand (IV) wherein n is 1 can be made by reacting methanesulfonyl chloride with an appropriate amine to form the sulfonamide, and then metalating the sulfonamide with n-butyl lithium and reacting with an appropriate diarylchlorophosphine.

For compounds wherein n is 2 or 3 the following synthesis applicable:

$Cl(CH_2)_{2-3}SO_2Cl + Ar'NH_2 \rightarrow Cl(CH_2)_{2-3}SO_2NHAr'$ $Cl(CH_2)_{2-3}SO_2NHAr' + Ar_2PNa \rightarrow Ar_2P(CH_2)_{2-3}SO_2NHAr'$ A reaction similar to the second reaction is described in European Patent Application 280,380.

Nickel complexes of the various phosphinosulfonamides can be made by a variety of methods. Bis(1,4-cyclooctadiene)Ni [0] may be reacted with the phosphinosulfonamide to form a complex useful as an oligomerization catalysts (see Example 6). The compound (N,N,N'N'-tetramethylethylenediamine)NiMe$_2$ may be reacted with the phosphinosulfonamide to form an active catalyst (see Examples 7 and 8).

Ligands to which ethylene may add to include hydride, alkyl, or $R^7C(=O)$— wherein $R^7$ is hydrocarbyl or substituted hydrocarbyl, and groups such as $\eta^3$-$C_8H_{13}$. Such groups are also described in World Patent Application WO 96/23010.

Nickel complexes containing hydride ligands can be made by the reaction of compounds such as (I) or (II) wherein $L^1$ is alkyl and $L^2$ is neutral ligand with hydrogen. The same starting materials, when treated with CO will form complexes with acyl ligands.

In ligands (II) and (IV) and in the corresponding complexes (I) and (III) the following groups are preferred:

R¹, R², R³, R⁴, R⁵ and R⁶ are hydrogen; and/or

R¹, R², R⁴, R⁵ and R⁶ are hydrogen and R³ is methyl; and/or n is 1; and/or

Ar¹ is 2,6-dimethylphenyl, 2,6-diisopropylphenyl, 2-isopropylphenyl, or 2,4,6-tri-t-butylphenyl; and/or Ar² and Ar³ are aryl or substituted aryl, preferably phenyl, 2-methylphenyl, or 3,5-bis(trifluoromethyl)phenyl, or alkyl or cycloalkyl containing 1 to 8 carbon atoms and/or [in (I) or (III) only]

L¹ is an alkyl nitrile, more preferably acetonitrile; and/or

L² is alkyl, preferably methyl; and/or

L¹ and L² taken together are η³-C₈H₁₃ [η³-(cycloocatdienyl)]

Similar groups are preferred in compounds (V), (VII), and (VIII), where appropriate.

Another useful ligand, similar to (VIII) is

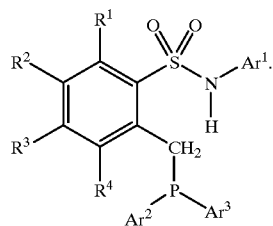

(IX)

In (IX) R¹, R², R³, R⁴, Ar¹, Ar² and Ar³ are as defined above, and (IX) may used as a ligand an in nickel complexes the same way as (VIII). In a preferred (IX), R² and R⁴ are hydrogen, R¹ and R³ are methyl, Ar¹ is 2,6-diisopropylphenyl and Ar² and Ar³ are phenyl.

Specific preferred compounds for (I), (II), (III) and (IV) are shown in the Table immediately below. R¹ through R⁶ are all hydrogen. Similar substitution is preferred in compounds (V), (VII) and (VIII), where appropriate.

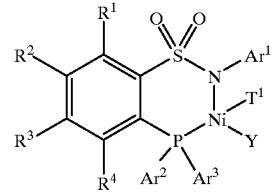

(V)

wherein R¹ through R⁴, Ar¹, Ar² and Ar³ are as defined above, T¹ is hydride, alkyl, or R⁷C(=O)— wherein R⁷ is hydrocarbyl or substituted hydrocarbyl, and Y is a neutral ligand. Similar complexes may also be formed with (IV). Such complexes may be added directly to the process or formed in situ. (V) may be added to the oligomerization as a preformed complex or be formed in situ. It may be made by reacting (1,2-dimethoxyethane)NiBr₂ with an alkali metal salt of a phosphinosulfonamide in the presence of acetonitrile to form

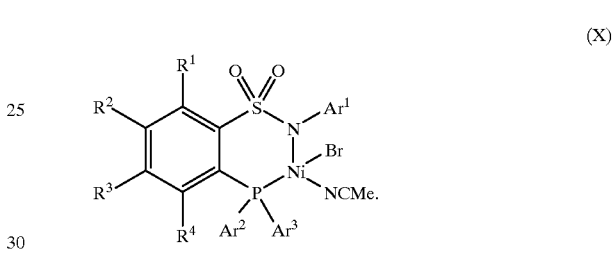

(X)

(X) may then be reacted with an alkylating compound such as an alkyl aluminum compound, for instance poly (methylaluminoxane), to form replace the bromine in (X) with a methyl group. This may be done beforehand to preform (V), or in situ, optionally in the presence of ethylene.

Another method of initiating polymerization is reaction of (tmeda)NiMe₂ with (VIII) or other similar phosphinosulfonamides.

| Compound | Ar¹ | Ar² and Ar³ | L¹ | L² | n |
|---|---|---|---|---|---|
| Ia | 2,6-diisopropylphenyl | phenyl | a | a | — |
| Ib | 2,6-diisopropylphenyl | phenyl | CH₃CN | CH₃ | — |
| IIIa | 2,6-diisopropylphenyl | phenyl | CH₃CN | CH₃ | 1 |
| IIa | 2,6-diisopropylphenyl | phenyl | — | — | — |
| IIb | 2,6-dimethylphenyl | phenyl | — | — | — |
| IIc | 2,4,6-tri-t-butylphenyl | phenyl | — | — | — |
| IId | 2,6-diisopropylphenyl | 2-methylphenyl | — | — | — |
| IIe | 2,6-diisopropylphenyl | 3,5-bis(trifluoromethyl)phenyl | — | — | — |
| IVa | 2,6-diisopropylphenyl | phenyl | — | — | 1 |

ᵃL¹ and L² taken together are η³-C₈H₁₃.

In the second polymerization process described herein a nickel [II] complex of (II) or (IV) is either added to the polymerization process or formed in situ in the process. In fact, more than one such complex may be formed during the course of the process, for instance formation of an initial complex and then reaction of that complex to form a living ended polymer containing such a complex.

An example of such a complex which may be formed initially in situ is

A Lewis acid may optionally be present during any of the polymerization processes herein. The Lewis acid may aid in producing polymer, by allowing the polymerization to proceed, to proceed at lower temperatures, and/or to produce a somewhat different polymer, such as a polymer with higher molecular weight. Whether the Lewis acid is effective in modifying the process can be determined by minimal experimentation, by simply attempting a polymerization as described in the Examples with the Lewis acid present.

It is preferred that the Lewis acid, if present, be one of moderate strength. Useful Lewis acids include (C₆F₅)₃B and (C₆H₅)₃B. A catalytically useful amount of the Lewis acid (if present) should be present. Preferably about 0.1 to about 200 moles, more preferably about 1 to about 100 moles, and especially preferably about 2 to about 50 moles of Lewis acid per mole of nickel compound should be present. The Lewis acid may added before, simultaneously with, or after the olefin(s) to be polymerized are added.

After the ethylene polymerization has started, the complex may be in a form such as

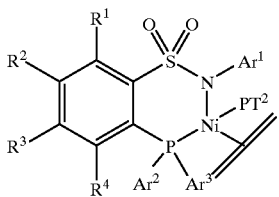

(VII)

wherein $R^1$ through $R^4$, $Ar^1$, $Ar^2$ and $Ar^3$ are as defined above, P is a divalent (poly)ethylene group, —$(CH_2)_x$—, wherein x is an integer of 2 or more, and $T^2$ is an end group, for example the groups listed for $T^1$ above. Similar complexes may also be formed with (IV).

In all the polymerization processes herein, the temperature at which the ethylene polymerization is carried out is about −20° C. to about +200° C., preferably about 0° C. to about 150° C., more preferably about 25° C. to about 100° C. The ethylene pressure at which the polymerization is carried out is not critical, atmospheric pressure to about 275 MPa being a suitable range. However elevated pressures, about 2 to about 100 MPa is preferred.

The polymerization processes herein may be run in the presence of various liquids, particularly aprotic organic liquids. The catalyst system, ethylene, and polyethylene may be soluble or insoluble in these liquids, but obviously these liquids should not prevent the polymerization from occurring. Suitable liquids include alkanes, cycloalkanes, selected halogenated hydrocarbons, and aromatic hydrocarbons. Specific useful solvents include hexane, toluene and benzene.

The catalysts herein may be "heterogenized" by coating or otherwise attaching them to solid supports, such as silica or alumina. Where an active catalyst species is formed by reaction with a compound such as an alkylaluminum compound, a support on which the alkylaluminum compound is first coated or otherwise attached is contacted with the nickel compound precursor to form a catalyst system in which the active nickel catalyst is "attached" to the solid support. These supported catalysts may be used in polymerizations in organic liquids, as described in the immediately preceding paragraph. They may also be used in so-called gas phase polymerizations in which the olefin(s) being polymerized are added to the polymerization as gases and no liquid supporting phase is present.

Included herein within the definitions of all the polymerization processes are mixtures of starting materials that lead to the formation in situ of the nickel compounds specified in all of the polymerization processes.

In the Examples, the following abbreviations are used:
Bu—butyl
COD—1,4-cyclooctadiene
Me—methyl
Mes—mesityl
OAc—acetate
Ph—phenyl
Pr—propyl THF—tetrahydrofuran
tmeda—N,N,N',N'-tetramethylethylenediamine In the Examples $^1H$ and $^{13}C$ NMR spectra were recorded on either a Varian XL-400, Gemini-300 or a Bruker WM-200 spectrometer. $^{31}P$ NMR spectra were recorded on a Gemini-300 spectrometer. NMR spectra were recorded using $CDCl_3$ solvent except where noted. $Ph_2PCl$ (Strem Chemical) was used as received. $Ar_2PCl$ (Ar=3,5-$(CF_3)_2C_6H_3$, 2-$MeC_6H_4$) was made by the procedure of Casalnuovo, A. L.; RajanBabu, T. V.; Ayers, T. A.; Warren, T. H. *J. Am. Chem. Soc.* 1994, 116, 9869–9882; (tmeda)$MgMe_2$ was made by the procedure of Coates, G. E.; Heslop, J. A. *J. Chem. Soc.* (A) 1966, 26–27; and (tmeda) $Ni(acac)_2$ was made by the procedure of Kaschube, W.; Pörschke, K. R.; Wilke, G. *J. Organomet. Chem.* 1988, 355, 525–532. NMR spectra are referenced relative to (residual) signals from the solvent. Coupling constants are reported in Hz and unless stated otherwise are C—H coupling constants.

Experiment A (tmeda)$NiMe_2$. The complex was synthesized by a variant of the published procedure. To a 250 mL 1-neck round bottom flask with Schlenk adapter was added 8.898 g (23.85 mmol) (tmeda)Ni(acac)$_2$ and 4.068 g (23.85 mmol) (tmeda) $MgMe_2$. The flask was cooled to −30° C. and 100 mL of diethyl ether was added via syringe. The resulting solution turned dark brown with vigorous bubbling. The solution was stirred at −30° C. for 1 h over which period yellow crystals precipitated. The reaction mixture was cooled to −50° C. and the supernatent was removed by cannula filtration. The crystals left behind were washed with 10 mL diethyl ether, dried under vacuum and stored in a freezer at −30° C. Yield: 3.413 g (70%).

Synthesis of Sulfonamides

Method A. Sulfonamides derived from arenesulfonyl chlorides were prepared in refluxing acetic acid (see Shepherd, R. G. *J. Org. Chem.* 1947, 12, 275–283).

Experiment B $PhSO_2NH(2,6-i-Pr_2C_6H_3)$

A 100 mL flask was charged with 16.225 g (91.5 mmol) 2,6-diisopropylaniline and 35 mL glacial HOAc. The flask was fitted with a reflux condenser and heated with a mantle. Once the solution was at reflux, 1.25 equiv benzenesulfonyl chloride (14.6 mL, 20.2 g, 114.4 mmol) was added. A total of 1.25 equiv NaOAc was added in portions (0.5, 0.25, 0.125, 0.125, 0.25) every 10–15 minutes. The solution turned cloudy on addition of NaOAc due to NaCl precipitate. Twenty minutes after the last addition of NaOAc distilled water was added until the solution was clear and then the solution was set aside to cool. Crystals of product formed on cooling which were washed with cold 60% HOAc (20 mL), cold 5 M HCl (20 mL) and cold $H_2O$ (20 mL). The crystals were dried under vacuum on a Schlenk line. Yield: 15.86 g, 55%. $^1H$ NMR: 7.71(Ar, 2H, dm, 7.1), 7.54(Ar, 1H, tt, 7.4, 1.3), 7.44(Ar, 2H, tm, 7.4), 7.25(Ar, 1H, dd, 7.8, 7.8), 7.09(Ar, 2H, d, 7.7), 6.11(NH, 1H, s), 3.09(CH, 2H, sept, 6.9), 0.98 $CH_3$, 12H, d, 6.8). $^{13}C$ NMR: 148.27, 140.25, 132.66, 129.02, 128.89, 128.77, 127.29, 123.90, 28.46, 23.75. Anal. Calcd. for $C_{18}H_{23}NO_2S$: C, 68.11; H, 7.30; N, 4.41. Found: C, 66.61; H, 6.90; N, 4.05.

Experiment C $PhSO_2NH(2,6-Me_2C_6H_3)$

Synthesized from 18.0 mL (17.7 g, 146 mmol) 2,6-dimethylaniline and 23.3 mL (32.2 g, 182.5 mmol) benzenesulfonyl chloride in 30 mL glacial HOAc. Yield: 28.95 g, 76%. $^1$H NMR: 7.70(Ar, 2H, br, m), 7.56(Ar, 1H, tt, 7.7, 1.4), 7.44(Ar, 2H, "t"m, 8.0), 7.07(Ar, 1H, dd, 8.5, 6.0), 6.99(Ar, 2H, d, br, 7.1), 6.04(NH, 1H, s), 2.01 (CH$_3$, 6H, s). $^{13}$C NMR: 140.54, 137.75, 132.80, 132.39, 128.99, 128.73, 127.83, 127.10, 18.62. Anal. Calcd. for C$_{14}$H$_{15}$NO$_2$S: C, 64.34; H, 5.79; N, 5.36. Found: C, 64.21; H, 5.81; N, 5.42.

Experiment D

PhSO$_2$NH(2-i-PrC$_6$H$_4$)

Synthesized from 15.45 g (114.3 mmol) 2-isopropylaniline and 18.2 mL (25.2 g, 142.9 mmol) benzenesulfonyl chloride in 30 mL glacial HOAc. Yield: 22.6 g, 72%. $^1$H NMR: 7.70(Ar, 2H, d, 8.1), 7.52(Ar, 1H, t, 7.4), 7.52(Ar, 2H, dd, 8.0, 7.5), 7.29(Ar, 1H, d, 7.8), 7.16(Ar, 2H, "t", 3.8), 7.11(Ar, 1H, br, m), 6.63(NH, 1H, s), 2.79(CH, 1H, sept, 6.9), 0.94(CH$_3$, 6H, d, 6.8). $^{13}$C NMR: 142.90, 139.41, 132.84, 132.46, 128.91, 127.19, 127.12, 126.42, 126.05, 125.80, 27.36, 23.17. Anal. Calcd. for C$_{15}$H$_{17}$NO$_2$S: C, 65.43; H, 6.22; N, 5.09. Found: C, 65.22; H, 6.28; N, 4.83.

Experiment E (Mes)SO$_2$NH(2,6-i-Pr$_2$C$_6$H$_3$)

Synthesized from 6.485 g (36.6 mmol) of 2,6-diisopropylaniline and 10.0 g (45.7 mmol) 2-mesitylenesulfonyl chloride in 20 mL glacial HOAc. Yield: 3.962 g (30%). $^1$H NMR: 7.24(Ar, 1H, t, 7.8), 7.08(Ar, 2H, d, 7.8), 6.90(Ar, 2H, s), 6.10(NH, 1H, s), 3.12(CH, 2H, sept, 6.8), 2.42(Me, 6H, s), 2.27(Me, 3H, s), 0.98(Me, 12H, d, 6.9). $^{13}$C NMR: 148.57, 142.11, 139.04, 135.27, 131.81, 129.39, 123.74, 28.42, 23.66, 23.13, 20.85.

Method B. Methane sulfonamides were prepared in methylene chloride at 0° C. (see Lis, R.; Marisca, A. J. *J. Org. Chem.* 1987, 52, 4377–4379).

Experiment F

MeSO$_2$NH(2,6-i-Pr$_2$C$_6$H$_3$)

A 300 mL 3-neck round bottom flask was charged with 6.24 g (35.2 mmol) 2,6-diisopropylaniline, 3.15 mL (3.08 g, 38.9 mmol) pyridine and 100 mL CH$_2$Cl$_2$. The solution was cooled to 0° C. and MeSO$_2$Cl was added via syringe. The solution turned yellow and it was allowed to warm to room temperature and stir overnight. The solution was extracted with 60 mL of 1 M NaOH then the organic layer was evaporated to dryness to yield an oil. The oil was dissolved in 300 mL of 50% aqueous ethanol and the resulting solution was concentrated on the rotary evaporator until colorless crystals precipitated. The product was collected on a fritted glass funnel and was washed with 20 mL cold ethanol (95%), 100 mL H$_2$O and 30 mL cold 35% aqueous ethanol. To dry the product, it was dissolved in a small amount of ether and dried over Na$_2$SO$_4$. The solution was filtered and evaporated to dryness to yield pure dry MeSO$_2$NH(2,6-i-Pr$_2$C$_6$H$_3$). Yield: 6.84 g (76%). $^1$H NMR: 7.30(Ar, 1H, t, 7.8), 7.18(Ar, 2H, d, 7.8), 5.82(NH, 1H, s), 3.47(CH, 2H, sept, 6.6), 3.07(CH$_3$, 3H, s), 1.22(CH$_3$, 12H, d, 6.8). $^{13}$C NMR: 148.12, 129.26, 129.01, 124.13, 41.13, 28.56, 24.01. Anal. Calcd. for C$_{13}$H$_{21}$NO$_2$S: C, 61.14; H, 8.29; N, 5.48. Found: C, 61.25; H, 8.29; N, 5.40.

EXAMPLE 1

2-Ph$_2$P(C$_6$H$_4$)SO$_2$NH(2,6-Me$_2$C$_6$H$_3$)

In a 250 mL round bottom flask was dissolved 3.428 g (13.1 mmol) PhSO$_2$NH(2,6-Me$_2$C$_6$H$_3$) in 50 mL dry THF under N$_2$. The resulting solution was cooled to 0° C. and 10.8 mL n-BuLi (2.5 M in hexanes, 26.9 mmol, 2.05 equiv) was added via syringe. A bright yellow suspension formed and was allowed to stir for 25 min. To this suspension was added 2.36 mL (2.90 g, 13.1 mmol) Ph$_2$PCl via syringe which caused the precipitate to dissolve and form an orange solution. After 1 min the reaction was quenched by the addition of 70 mL of cold water. Two layers formed and were separated. The organic layer was concentrated to give an orange gum. The gum was taken up in 80 mL of 95% ethanol to give a solution from which colorless crystals precipitated on standing. To remove all water and ethanol the crystals were dried in the melt under vacuum at 135° C. for 14 h. Yield: 2.227 g (38%). $^1$H NMR: 7.92(Ar, 1H, ddd, 7.6, 3.7, 1.6), 7.5–6.9(Ar, NH, 19H, br, m), 2.17(CH$_3$, 6H, s). $^{13}$C {$^1$H, $^{31}$P} NMR: 147.07, 138.15, 136.27, 135.66, 135.61, 133.67, 133.17, 132.19, 129.36, 129.06, 128.65, 128.52, 128.43, 127.85, 19.22. $^{31}$P NMR: −9.49 (s). Anal. Calcd. for C$_{26}$H$_{24}$NO$_2$PS: C, 70.10; H, 5.43; N, 3.14. Found: C, 71.71; H, 5.60; N, 3.22.

EXAMPLE 2

2-Ph$_2$P(C$_6$H$_4$)SO$_2$NH(2,6-i-Pr$_2$C$_6$H$_3$)

Synthesized from 8.84 g (27.8 mmol) PhSO$_2$NH(2,6-i-Pr$_2$C$_6$H$_3$), 22.3 mL n-BuLi (2.5 M in hexanes, 55.7 mmol, 2.05 equiv) and 5.00 mL (6.14 g, 27.8 mmol) Ph$_2$PCl in 100 mL of THF, in a manner similar to that of Example 1. Yield: 8.25 g (57%). $^1$H NMR: 7.94(Ar, 1H, br, m), 7.5–7.1(Ar, NH, 17H, br, m), 3.30(CH, 2H, sept, 6.8), 1.04(CH$_3$, 12H, d, 6.8). $^{13}$C {$^1$H, $^{31}$P} NMR: 148.78, 146.75, 136.27, 135.66, 135.46, 133.61, 132.10, 129.66, 129.24, 129.06, 128.77, 128.71, 128.63, 123.92, 28.90, 24.00. $^{31}$P NMR: −9.85 (s). Anal. Calcd. for C$_{30}$H$_{32}$NO$_2$PS: C, 71.83; H, 6.43; N, 2.79. Found: C, 72.01; H, 6.45; N, 2.85.

EXAMPLE 3

2-[(3,5-(CF$_3$)$_2$C$_6$H$_3$)$_2$P](C$_6$H$_4$)SO$_2$NH(2,6-i-Pr$_2$C$_6$H$_3$)

Synthesized from 2.442 g (7.69 mmol) PhSO$_2$NH(2,6-i-Pr$_2$C$_6$H$_3$) in 30 mL THF, 6.3 mL n-BuLi (2.5 M in hexanes, 15.8 mmol, 2.05 equiv) and 3.782 g (7.69 mmol) (3,5-(CF$_3$)$_2$C$_6$H$_3$)$_2$PCl in 10 mL THF, in a manner similar to that of Example 1. Yield: 4.22 g (71%). $^1$H NMR: 8.08–7.98 (Ar, 2H, br, m), 7.93(Ar, 2H, s), 7.63(Ar, 2H, d, 6.9), 6.76(NH, 1H, s), 3.20(CH, 2H, sept, 6.6), 1.02(CH$_3$, 12H, d, 6.6). $^{31}$P NMR: −7.82 (s). $^{19}$F NMR: −63.86 (s).

EXAMPLE 4

2-[(2-Me-C$_6$H$_4$)$_2$P](C$_6$H$_4$)SO$_2$NH(2,6-i-Pr$_2$C$_6$H$_3$)

Synthesized from 6.11 g (19.26 mmol) PhSO$_2$NH(2,6-i-Pr$_2$C$_6$H$_3$) in 70 mL THF, 15.8 mL n-BuLi (2.5 M in hexanes, 39.5 mmol, 2.05 equiv) and 4.79 g (19.26 mmol) (3,5-(CF$_3$)$_2$C$_6$H$_3$)$_2$PCl in 10 mL THF, in a manner similar to that of Example 1. NMR spectral analysis consistent with two rotational isomers present in a ca. 7:1 ratio. Yield: 7.15 g (70%). $^1$H NMR (major product): 7.93(Ar, 1H, br, m), 7.38(Ar, 2H, br, m), 7.25–6.9(Ar, 10H, br), 6.69(Ar, 2H, br, m), 3.14(CH, 2H, sept, 7.0), 2.29(CH$_3$, 6H, s), 1.00(CH$_3$, 12H, d, 7.0). $^{31}$P {$^1$H} NMR: −19.09 (minor), −23.46 (major).

EXAMPLE 5

Ph$_2$PCH$_2$SO$_2$NH(2,6-i-Pr$_2$C$_6$H$_3$)

Synthesized from 4.363 g (17.1 mmol) MeSO$_2$NH(2,6-i-Pr$_2$C$_6$H$_3$) in 100 mL THF, 14.0 mL n-BuLi (2.5 M in hexanes, 35.0 mmol, 2.05 equiv) and 3.07 mL (3.77 g, 17.1 mmol) Ph$_2$PCl. Recrystallized from 300 mL 50 % aqueous ethanol. Yield: 2.88 g (38%). $^1$H NMR: 7.5–7.0(Ar, 13H, m, br), 5.98(NH, 1H, s), 3.94(CH$_2$, 2H, s), 3.30(CH, 2H, sept, 7.0), 1.02(CH$_3$, 12H, d, 7.0). $^{13}$C NMR: 148.26, 136.26(d, 10.8), 132.90(d, 20.6), 129.67, 129.54, 128.97, 128.85(d, 7.6), 124.05, 57.08(d, 32.5), 28.78, 23.90. $^{31}$P NMR: −22.82 (s). Anal. Calcd. for C$_{25}$H$_{30}$NO$_2$PS: C, 68.31; H, 6.88; N, 3.19. Found: C, 67.85; H, 6.89; N, 3.14.

EXAMPLE 6

[2-Ph$_2$P(C$_6$H$_4$)SO$_2$N(2,6-i-Pr$_2$C$_6$H$_3$)]Ni($\eta^3$-C$_8$H$_{13}$)

A 50 mL round bottom flask was charged with 437 mg (1.59 mmol) (cod)$_2$Ni and 797 mg (1.59 mmol) 2-Ph$_2$P(C$_6$H$_4$)SO$_2$NH(2,6-i-Pr$_2$C$_6$H$_3$). The solids were dissolved in 10 mL toluene and the resulting burgundy solution was allowed to stir overnight. The product was precipitated as a red-orange powder by adding 10 mL hexanes. The powder was isolated by filtration and was washed with hexanes (3×5 mL). The dried product weighed 645 mg (61% yield). The $^{31}$P NMR spectrum suggested the presence of two similar products in a 7:1 ratio which may reflect two coordination modes of the $\eta^3$-C$_8$H$_{13}$ group (allyl and 4-enyl) (see Peuckert, M.; Keim, W. *Organometallics* 1983, 2, 594–597). $^{31}$P NMR: 27.39(s, minor), 26.60(s, major).

EXAMPLE 7

[2-Ph$_2$P(C$_6$H$_4$)SO$_2$N(2,6-i-Pr$_2$C$_6$H$_3$)]NiMe(MeCN)

A Schlenk flask was charged with 823 mg (4.02 mmol) (tmeda)NiMe$_2$ and 2115 mg (4.22 mmol) 2-Ph$_2$P(C$_6$H$_4$)SO$_2$NH(2,6-i-Pr$_2$C$_6$H$_3$) and cooled to −30° C. To the solids were added 50 mL toluene which produced a red solution. Acetonitrile (2.2 mL, 42.2 mmol) was added which caused the solution to change to brownish amber. The solution was stirred 1 h at room temperature over which time a yellow precipitate formed. The product was isolated by cannula filtration and was washed with hexanes (2×8 mL). The powder was dried under vacuum to afford 2058 mg [2-Ph$_2$P(C$_6$H$_4$)SO$_2$N(2,6-i-Pr$_2$C$_6$H$_3$)]NiMe(MeCN)·(toluene) (83%). The mother liquor and washings were combined and concentrated. From the concentrate was recovered an additional 58 mg product (total yield 2116 mg, 86%). $^1$H NMR (C$_6$D$_6$): 8.2–7.8(Ar, br, 4H), 7.3–6.6(Ar, br, 18H), 4.65(CH, br, 2H), 2.28(PhC$\underline{H}_3$, s, 3H), 1.6(CH$_3$, br, 12H), 0.46 (MeCN, s, 3H), 0.02(NiCH$_3$, d, J$_{PH}$ 7 Hz) $^{31}$P NMR: (C$_6$D$_6$): 15.80(s). Anal. Calcd. for C$_{33}$H$_{37}$N$_2$NiO$_2$PS: C, 64.41; H, 6.06; N, 4.55. Found: C, 61.87; H, 5.98; N, 4.21.

EXAMPLE 8

[Ph$_2$PCH$_2$SO$_2$N(2,6-i-Pr$_2$C$_6$H$_3$)]NiMe(MeCN)

A Schlenk flask was charged with 192 mg (0.937 mmol) (tmeda)NiMe$_2$ and 432 mg (0.984 mmol) Ph$_2$PCH$_2$SO$_2$NH (2,6-i-Pr$_2$C$_6$H$_3$) and cooled to −30°C. Toluene (15 mL) and acetonitrile (1 mL, 19.15 mmol) were added which resulted in a brown solution. The solution was allowed to warm to room temperature and a small amount of yellow precipitate was observed. Hexanes (10 mL) were added and the solution was cooled to −30° C. which resulted in the formation of yellow feathery crystals. The crystals were isolated by cannula filtration and were washed with hexanes (2×10 mL). After drying under vacuum, 273 mg (yield 45%) [Ph$_2$PCH$_2$SO$_2$N(2,6i-Pr$_2$C$_6$H$_3$)]NiMe(MeCN)·(toluene) was recovered. $^1$H NMR (C$_6$D$_6$): 7.88(Ar, 4H, br), 7.05(Ar, 9H, br), 4.48 (CH, 2H, br), 3.63 (CH$_2$, 2H, d, $^2$J$_{PH}$=6.9), 1.45(CHC$\underline{H}_3$, 6H, d, 6.3), 1.33(CHC$\underline{H}_3$, 6H, d, 6.3), 0.22 (NCCH$_3$, 3H, s), −0.26(NiCH$_3$, 3H, d, $^2$J$_{PH}$=6.0). $^{31}$P NMR (C$_6$D$_6$): 17.23 (s).

EXAMPLES 9–18

Oligomerization experiments were carried out under ethylene pressure in a stainless steel Parr® Model 4521 stainless steel reactor with a volume of 1000 mL. Unless otherwise noted, the reactions were run in 180 mL toluene with a catalyst concentration of ca. 2 mM. The reaction time was 210 min. At the end of that time the reactor was vented, cooled, and opened. The reaction solution was poured into an equal volume of acetone which usually caused oligomeric product to precipitate. In most cases the precipitated product could not be collected by filtration (clogged) and instead the reaction mixture was washed with water and concentrated with a rotary evaporator.

The products were analyzed by $^1$H NMR spectroscopy which was used to determine the average DP (degree of polymerization, the average number of repeat units in a polymer molecule), branching (branches per 1000 total methylene groups, corrected for end groups), the mole percent α-olefin in the mixture, turnovers (TO) the number of moles of ethylene polymerization per g-atom of nickel present, and TO/h the number of moles of ethylene polymerized per h averaged over the course of the oligomerization. Because of the method for sample workup, oligomers C$_{10}$ and lower were assumed to be lost. The data in Table 1 are the values for the recovered product.

TABLE 1

| Ex. No. | Catalyst System Exp. or Ex. No., and/or Ni Compound[a] | p (atm) | T(° C.) | TO/h | TO | % α | branching | DP |
|---|---|---|---|---|---|---|---|---|
| 9 | (COD)$_2$Ni + Ex 1 | 1 | RT→50 | 20 | 120 | 0 | 12 | 7 |
| 10 | (COD)$_2$Ni + Ex. 2 | 27 | 50 | 545 | 1900 | 18 | 26 | 16 |
| 11 | Ex. 6 | 27 | 50 | 50 | 155 | 18 | 30 | 20 |
| 12 | Ex 6 | 54 | 80 | 105 | 315 | 24 | 47 | 15 |
| 13 | (COD)$_2$Ni + Ex. 2 | 27 | 50 | 900 | 3140 | 18 | 20 | 14 |
| 14 | (COD)$_2$Ni + Ex. 3 | 27 | 50 | 760 | 2700 | 13 | 18 | 14 |
| 15 | (COD)$_2$Ni + Ex. 1 | 27 | 50 | 2150 | 7550 | 19 | 45 | 11 |
| 16 | (COD)$_2$Ni + Ex. 4 | 27 | 50 | 25 | 90 | 4 | 22 | 9 |
| 17 | Ex. 7 | 41 | 45 | 380 | 1140 | 18 | 12 | 25 |
| 18 | Ex. 8 | 41 | 50 | 2550 | 8900 | 35 | 25 | <25[b] |

[a]Source of Ni compound and ligand.
[b]Fifteen g of a solid wax with average DP = 25 was isolated on filter paper. The lower molecular weight liquid was not analyzed.

What is claimed is:

1. A compound of the formula

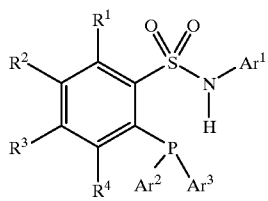
(VIII)

wherein:
- $R^1$, $R^2$, $R^3$ and $R^4$ are each independently hydrogen, hydrocarbyl, substituted hydrocarbyl, or an inert functional group;
- $R^5$ and $R^6$ are each independently hydrogen, hydrocarbyl or substituted hydrocarbyl; and
- $Ar^1$ is aryl or substituted aryl
- $Ar^2$ and $Ar^3$ are each independently hydrocarbyl or substituted hydrocarbyl.

2. A compound of the formula

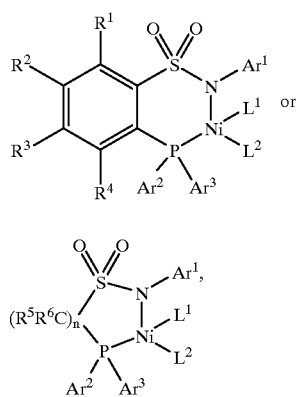
(I)

(III)

wherein:
- $R^1$, $R^2$, $R^3$ and $R^4$ are each independently hydrogen, hydrocarbyl, substituted hydrocarbyl, or an inert functional group;
- $R^5$ and $R^6$ are each independently hydrogen, hydrocarbyl or substituted hydrocarbyl;
- n is 1, 2 or 3;
- $Ar^1$ is aryl or substituted aryl
- $Ar^2$ and $Ar^3$ are each independently hydrocarbyl or substituted hydrocarbyl; and
- $L^1$ is a neutral monodentate ligand and $L^2$ is a monoanionic monodentate ligand, or $L^1$ and $L^2$ taken together are a monoanionic bidentate ligand, provided that said monoanionic monodentate ligand or said monoanionic bidentate ligand may be displaced by said ethylene or add to said ethylene.

3. The compound as recited in claim 1 or 2 wherein n is 1.

4. The compound as recited in claim 1 or 2 wherein $R^1$, $R^2$, $R^3$, $R^4$, $R^5$ and $R^6$ are all hydrogen.

5. The compound as recited in claim 3 wherein $R^1$, $R^2$, $R^3$, $R^4$, $R^5$ and $R^6$ are all hydrogen.

6. The compound as recited in claim 5 wherein:
- $Ar^1$ is 2,6-dimethylphenyl, 2,6-diisopropylphenyl, 2-isopropylphenyl, or 2,4,6-tri-t-butylphenyl; and
- $L^1$ is an alkyl nitrile and $L^2$ is alkyl, or $L^1$ and $L^2$ taken together are $\eta^3$-$C_8H_{13}$.

7. The compound as recited in claim 6 wherein $L^1$ is acetonitrile and $L^2$ is methyl.

8. The compound as recited in claim 1 or 2 wherein $Ar^2$ and $Ar^3$ are aryl or substituted aryl.

* * * * *